US 6,379,679 B1

(12) United States Patent
Mabrouk et al.

(10) Patent No.: US 6,379,679 B1
(45) Date of Patent: Apr. 30, 2002

(54) MULTIPLE BRANCH PEPTIDE CONSTRUCTION

(75) Inventors: Kamel Mabrouk, Marseilles; Jean-Marc Sabatier, Chateauneuf-le-Rouge; Herve Rochat, Mimet; Jurphaas Van Rietschoten, Aix-en-Provence, all of (FR)

(73) Assignee: Gellpep S.A., Paris (FR)

( * ) Notice: Subject to any disclaimer, the term of this patent is extended or adjusted under 35 U.S.C. 154(b) by 0 days.

(21) Appl. No.: 09/342,847

(22) Filed: Jun. 29, 1999

Related U.S. Application Data

(63) Continuation of application No. PCT/EP97/07334, filed on Dec. 30, 1997.

(30) Foreign Application Priority Data

Dec. 31, 1996 (GB) .............................................. 9627114

(51) Int. Cl.[7] .............................................. A61K 45/00
(52) U.S. Cl. ............................... 424/281.1; 424/184.1; 424/188.1; 424/194.1; 424/278.1; 514/2; 530/323; 530/328; 530/329; 530/330; 530/333; 530/334; 530/335
(58) Field of Search .......................... 530/323, 324–330, 530/332, 333–337, 806, 826; 424/184.1, 185.1, 186.1, 188.1, 194.1, 278.1, 281.1; 514/2

(56) References Cited

U.S. PATENT DOCUMENTS 5,229,490 A * 7/1993 Tam ........................... 530/324
5,556,744 A * 9/1996 Weiner et al. ................. 435/5

OTHER PUBLICATIONS

Sabatier et al. "Anti–HIV Activity of Multibranched Peptide Constructs Derived Either from The Cleavage Sequence or from the Transmembrane Domain (Gp41) of the Human Immunodeficiency Virus Type 1 Envelope", Virology, vol. 223, No. 2 (1996)., pp. 406–408. QR1.V5.*

Benjouad et al. "Multibranched Peptide Constructs Derived from the V3 Loop of Envelope Glycoprotein gp120 Inhibit Human Immunodeficiency Virus Type 1 Infection through Interaction with CD4" Virology, vol. 206, No. 1(1995), pp. 457–464. QR1. V5.*

* cited by examiner

Primary Examiner—Jeffrey Stucker
(74) Attorney, Agent, or Firm—Cherskov & Flaynik

(57) ABSTRACT

Multiple branch peptide constructions formed from peptides derived from the envelope transmembrane glycoprotein gp41 of HIV, and including the consensus sequence RQGY preceded by 0 to 4 amino acid residues and succeeded by 2 to 4 amino acid residues, most preferably RQGYSPL, show increased receptor affinity and prevent cell-to-cell fusion. They have a direct virostatic effect. Because they present the same peptide sequence several times, these MBPCs are able to neutralize in vitro the different steps of virus envelope/cell membrane fusion, and infected cell membrane/uninfected cell membrane fusion of several strains of HIV-1 and HIV-2. These results open a potential use in treatment of HIV infection.

19 Claims, No Drawings

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
       (A) LENGTH: 4 amino acids
       (B) TYPE: amino acid
       (C) STRANDEDNESS: <Unknown>
       (D) TOPOLOGY: linear (ii) MOLECULE TYPE: Genomic DNA (iii) HYPOTHETICAL: yes (xi) SEQUENCE DESCRIPTION: SEQ ID NO: 1

Arg Gln Gly Tyr
1

(2) INFORMATION FOR SEQ ID NO: 2:

(i) SEQUENCE CHARACTERISTICS:
        (A) LENGTH: 7 amino acids
        (B) TYPE: amino acids
        (C) STRANDEDNESS: <Unknown>
        (D) TOPOLOGY: linear (ii) MOLECULE TYPE: Genomic DNA (iii) HYPOTHETICAL: yes (xi) SEQUENCE DESCRIPTION: SEQ ID NO: 2:

Arg Gln Gly Tyr Ser Pro Leu
 1               5

(2) INFORMATION FOR SEQ ID NO: 3:

(i) SEQUENCE CHARACTERISTICS:
        (A) LENGTH: 64 amino acids
        (B) TYPE: amino acids
        (C) STRANDEDNESS: <Unknown>
        (D) TOPOLOGY: linear (ii) MOLECULE TYPE: Genomic DNA (iii) HYPOTHETICAL: yes (xi) SEQUENCE DESCRIPTION: SEQ ID NO: 3:

Arg Gln Gly Tyr Ser Pro Leu Arg Gln Gly Tyr Ser Pro Leu Arg Gln
 1               5                  10                  15

Gly Tyr Ser Pro Leu Arg Gln Gly Tyr Ser Pro Leu Arg Gln Gly Tyr
                20                  25                  30

Ser Pro Leu Arg Gln Gly Tyr Ser Pro Leu Arg Gln Gly Tyr Ser Pro
            35                  40                  45

Leu Arg Gln Gly Tyr Ser Pro Leu Lys Lys Lys Lys Lys Lys Lys Ala
        50                  55                  60

(2) INFORMATION FOR SEQ ID NO: 4:

(i) SEQUENCE CHARACTERISTICS:
        (A) LENGTH: 128 amino acids
        (B) TYPE: amino acids
        (C) STRANDEDNESS: <Unknown>
        (D) TOPOLOGY: linear (ii) MOLECULE TYPE: Genomic DNA (iii) HYPOTHETICAL: yes (xi) SEQUENCE DESCRIPTION: SEQ ID NO: 4:

Arg Gln Gly Tyr Ser Pro Leu Arg Gln Gly Tyr Ser Pro Leu Arg Gln
 1               5                  10                  15

Gly Tyr Ser Pro Leu Arg Gln Gly Tyr Ser Pro Leu Arg Gln Gly Tyr
                20                  25                  30

Ser Pro Leu Arg Gln Gly Tyr Ser Pro Leu Arg Gln Gly Tyr Ser Pro
            35                  40                  45

Leu Arg Gln Gly Tyr Ser Pro Leu Arg Gln Gly Tyr Ser Pro Leu Arg
        50                  55                  60

Gln Gly Tyr Ser Pro Leu Arg Gln Gly Tyr Ser Pro Leu Arg Gln Gly
 65                  70                  75                  80

Tyr Ser Pro Leu Arg Gln Gly Tyr Ser Pro Leu Arg Gln Gly Tyr Ser
                85                  90                  95

-continued

```
Pro Leu Arg Gln Gly Tyr Ser Pro Leu Arg Gln Gly Tyr Ser Pro Leu
            100                 105                 110

Lys Lys Lys Lys Lys Lys Lys Lys Lys Lys Lys Lys Lys Lys Lys Ala
            115                 120                 125
```

MULTIPLE BRANCH PEPTIDE CONSTRUCTION

This application claims priority under 35 U.S.C. §371 of International Patent Application Number PCT/EP97/07334, filed Dec. 30, 1997.

BACKGROUND OF THE INVENTION

1. Field of the Invention

The invention relates to multiple branch peptide constructions (MBPCs) and to their use in the treatment of Human Immunodeficiency Virus (HIV) infections.

2. Background of the Invention

The use of radially branched systems in polymers has been known for a long time in classical polymer chemistry. This system has been used by J. P. Tam [*Proc. Natl. Acad. Sci. USA* 85, 5409–5413 (1988)] to develop antigens without the use of ambiguous carriers, using lysine skeletons. Those antigens were designed to generate vaccines against a variety of diseases. Antigens for generating vaccines against HIV infection are described by Tam in WO93/03766. He called them Multiple Antigenic Peptide Systems (MAPS), consistent with their conceived use.

The present inventors, along with others, found that similar constructions with shorter peptides derived from the V3 loop of the surface envelope glycoprotein gp120 of HIV offered a direct therapeutic approach to the treatment of HIV infections, as described in WO95/07929. The name MAPS was then inappropriate, and the compounds were renamed as MBPCs. The MBPCs of WO95/07929 interfered with the virus envelope—cell membrane fusion step and also the infected cell membrane—uninfected cell membrane fusion step, either step being thought to be indispensable for cell infection, virus multiplication and the spread of virus in the host organism, by blockading the CD4 receptor present in cells such as lymphocytes and macrophages, apparently by attaching to a membrane co-receptor which is distinct from the CD4 binding receptor, without causing the cell to lose its ability to be activated by other antigens or mitogens.

DETAILED DESCRIPTION OF THE INVENTION

The inventors have now discovered further MBPCs which are effective as treatments for HIV infections. These use peptides derived from the HIV envelope transmembrane glycoprotein gp41. The amino acid sequences of these MBPCs were selected on the basis of sequence homologies between various HIV isolates. The choice of gp41 amongst viral proteins was based on the following:

i) the importance of this domain in the virus-cell and cell-cell fusion processes leading to virus entry into the host cell, ii) the importance of the gp160 splicing into gp120 and gp41 for the fusogenic activity to take place, iii) the existence of neutralizing anti-gp41 antibodies, e.g. antibody 2F5, and iv) the existence of a unique disulphide bridge, in contrast to gp120, which makes it easier to obtain peptides mimicking specific conformational domains of gp41.

It is presumed that the gp41-derived MBPCs of this invention interfere with a critical step of the fusion process.

The invention provides a multiple branch peptide construction and a method for the therapeutic treatment of patients with HIV infections. The multiple branch peptide construction comprises a core matrix to which are bonded from 2 to 16, and preferably from 4 to 16 peptides, each of which comprises the sequence RQGY (SEQ. ID NO. 1) preceded by from 0 to 4 amino acid residues and succeeded by from 2 to 4 amino acid residues. Preferably, the peptides bonded to an 8 or 16-branched core matrix are RQGYSPL (SEQ. ID. NO. 2). The method for the therapeutic treatment of patients with HIV infections comprises administering such an MBPC to the patient, preferably in such an amount as to induce in the patient a blood concentration of the MBPC of from $10^{-7}$ to $10^{-4}$ molar.

The core matrix is a dendritic polymer which is branched in nature, preferably with each of the branches thereof being identical. The core matrix is based on a core molecule which has at least two functional groups to which molecular branches having terminal functional groups are covalently bonded. Suitable core molecules include ammonia or ethylenediamine. Suitable molecular branches include acrylic ester monomers which are polymerized onto the core molecule. Such molecules may be created to present varying number of branches, depending on the number of monomers branched from the core molecule. The preferred core molecule is lysine. A central lysine residue is bonded to two lysine residues, each through its carboxyl group, to one of the amino groups of the central lysine residue. This provides a molecule with four amino groups, which may be the core matrix for an MBPC having four peptides. Alternatively, one can provide a molecule with eight branches by bonding four lysine residues through their carboxyl groups to one of the amino groups of the lysine residues which are attached to the central lysine. This molecule can serve as the core matrix for an MBPC having eight peptides or can alternatively receive eight lysine residues to form a core matrix for an MBPC having sixteen peptides.

The C-ends of peptides are covalently bonded to each of the branches of the core matrix to form the MBPC. The peptides may be the same, which is preferred, or may be different from one another. The resulting molecule has a cluster of peptides at the surface and an interior core matrix which is not presented and is therefore notantigenic.

Spacers may, if desired, be included between the peptides and the core matrix. The carboxyl group of the first lysine residue may be left free, amidated, or coupled to β-alanine or another blocking compound.

Peptides can include D or L-amino acid residues. D amino acids last longer in vivo because they are harder for peptidase to cut, but the L amino acids have better activity, as discussed below.

Moreover, peptide analogues, synthetic constructs using the carbon skeleton of peptides but omitting the —CONH— peptide bonds, can be employed in place of peptides. Thus, it should be understood that references to peptides herein may also be taken to include peptide analogues. It is believed that peptide analogues will be more resistant to peptidase and last longer in vivo.

If the peptide is too long, the MBPC will become antigenic. It is therefore desirable that each peptide should have not more than ten, and preferably not more than nine, amino acid residues.

The preferred MBPCs for use in this invention are

RL.1: $(RQGYSPL)_8$—$(K)_4$—$(K)_2$—K—βA-(SEQ. ID. NO. 3) OH and

RL.2: $(RQGYSPL)_{16}$—$(K)_8$—$(K)_4$—$(K)_2$—K-βA-(SEQ. ID. NO. 4) OH

The OH terminal shown above on the β-alanine indicates the carboxyl group thereof, with the amino group being attached to the carboxyl group of the lysine residue. The carboxyl group of the β-alanine may alternatively be modified to form a carboxamide terminal.

The preparation of the MBPCs of the invention, having a branched core with peptides attached thereto, can be effected by methods known in the art, see e.g. Tam et al, J. Immun. 148, 914–920 (1992). Preferably, for small quantities (under one kilogram), a solid phase method is used to obtain the MBPCs. Stepwise assembly of the peptide chains can be carried out automatically on 4-(oxymethyl)-phenylacetamidomethyl copoly(styrene-1% divinyl benzene). The Boc/benzyl strategy may be used, including a systematic double coupling scheme with hydroxybenzotriazole active esters (Boc-amino-acid-OBt). The final cleaving from resin is effected with strong acid, such as anhydrous hydrogen fluoride (1 hour at 0° C.). The MBPC is then washed with diethyl ether and solubilized in water. After lyophilization, the MBPC may be pre-purified on a P2 or G15 type molecular filtration column, equilibrated with 0.1N acetic acid. The eluate fraction may then be recovered. The purification step is achieved by using $C_8$ or $C_{18}$ reversed-phase HPLC. The MBPC may be characterized by its amino acid content after acid hydrolysis (6N HCl, 115° C., 24 hours) and electrospray mass spectrometry.

The gp41-derived MBPCs of the invention have been tested in vitro for their ability to inhibit HIV-induced syncytium formation, and infection of human lymphocytes by both HIV-1 and HIV-2 viruses (several laboratory strains including LAV-2/B, an HIV-2 virus able to infect some CD4$^-$/GalCer$^-$ cells, as well as clinical isolates such as JRCSF, P16/B6 and P16/C9). The diverse peptide constructions were found to be inactive, except for MBPC RL1 which possessed potent antiviral properties in all tests. By contrast, the monomeric RQGYSPL (SEQ. ID. NO. 2) was found to be inactive. Some results are shown in Tables 1 and 2 below. Similar results were obtained with other HIV strains and clinical isolates tested so far.

The MBPC RL1 showed neither cellular toxicity nor lethal activity when injected by the intracerebroventricular route in both C57/BL6 and Balb-C mice (concentration tested was $3\times10^{-3}$ M, corresponding to 100 µg of peptide injected per 20 g mouse).

TABLE 1

Inhibition of the Hx10 (HIV-1) strain infectivity by the MBPCs RL1 and SPC3

| Peptides | Molarity | OD | p24 (ng/ml) | Inhibition (%) |
|---|---|---|---|---|
| SPC3-D4 | $5 \times 10^{-5}$ | 0.052 | 0.05556143 | 98.89 |
|  | $1 \times 10^{-5}$ | 0.211 | 0.48654334 | 89.13 |
|  | $5 \times 10^{-6}$ | 0.849 | 2.21589212 | 50.78 |
|  | $1 \times 10^{-6}$ | 1.797 | 4.78552009 | 0 |
| SPC3-D5 | $5 \times 10^{-5}$ | 0.066 | 0.09350952 | 98.47 |
| RL1-D4 | $5 \times 10^{-5}$ | 0.047 | 0.04200854 | 99.09 |
|  | $1 \times 10^{-5}$ | 0.359 | 0.88770888 | 79.82 |
|  | $5 \times 10^{-6}$ | 0.657 | 1.69546114 | 61.45 |
|  | $1 \times 10^{-6}$ | 1.148 | 3.02635495 | 31.29 |
| RL1-D5 | $5 \times 10^{-5}$ | 0.035 | 0.00948160 | 99.75 |

SPC3 is (GPGRAF)$_8$—(K)$_4$—(K)$_2$—K-βA-(SEQ. ID. NO. 3) OH as disclosed in WO95/07929.
D4 and D5 refer to days 4 and 5 of the experiment.
OD stands for Optical Density.
N.B. Experiments were performed with non diluted virus solution.

TABLE 2

Inhibition (%) of clinical isolates infectivity by the MBPCs RL1 and SPC3.

| [conc] | $1 \times 10^{-5}$ | $5 \times 10^{-6}$ | $1 \times 10^{-6}$ | $5 \times 10^{-7}$ | $1 \times 10^{-7}$ | $5 \times 10^{-8}$ |
|---|---|---|---|---|---|---|
| SPC3 | 85.7 | 50.0 | 28.6 | 0 | 0 | 0 |
| RL1 | 89.3 | 70.0 | 67.1 | 40.8 | 18.3 | 0 |

Example shown is the HIV-1 W5A2A9 isolate.
N.B. Experiments were performed with non diluted virus solution.

The embodiment of the invention in which an exclusive property or privilege is claimed is defined as follows:

1. A multiple branch peptide construct comprising a plurality of peptides limited to 10 or less amino acids, each or the peptides containing the amino acid sequence Arg-Gln-Gly-Tyr (SEQ. ID. NO. 1) and preceded by 0 to 4 amino acid residues and succeeded by from 2 to 4 amino acid residues.

2. The construct as recited in claim 1 wherein the peptides are attached to a core matrix.

3. The construct as recited in claim 1 wherein each peptide is the same.

4. The construct as recited in claim 1 wherein each peptide is Arg-Gln-Gly-Tyr-Ser-Pro-Leu (SEQ. ID. NO. 2).

5. The construct as recited in claim 1 wherein there are from 8 to 16 peptides, each peptide containing the sequence Arg-Gln-Gly-Tyr-Ser-Pro-Leu (SEQ. ID NO. 2).

6. The construct as recited in claim 2 wherein the core matrix is comprised of lysine residues.

7. The construct as recited in claim 2 wherein spacers exist intermediate the core matrix and the peptides.

8. The construct as recited in claim 1 wherein the peptides include peptide analogues.

9. The construct as recited in claim 1 wherein the peptides include at least one D-amino acid residue.

10. The construct as recited in claim 2 wherein said construct is non-immunogenic at a blood concentration of up to $10^{-4}$ molar.

11. The construct as recited in claim 2 wherein said construct is combined with a pharmaceutically acceptable carrier to form a medicament.

12. A method for treating HIV infections comprising administering to a patient a multiple branch peptide construct having a plurality of peptides, each of the peptides containing the amino acid sequence Arg-Gln-Gly-Tyr (SEQ. ID. NO. 1) preceded by 0 to 4 amino acids and succeeded by from 2 to 4 amino acids.

13. The method as recited in claim 12 wherein the construct is administered to the patient in an amount sufficient to induce in the patient a peptide blood concentration of less than $10^{-4}$ molar.

14. The method as recited in claim 12 wherein the plurality of peptides is attached to a core matrix.

15. The method as recited in claim 12 wherein the multiple branch construct is mixed with a pharmaceutically-acceptable carrier to form a medicament which is administered to the patient in an amount to induce in the patient a blood concentration of the multiple branch peptide construct of less than $10^{-4}$ molar.

16. A method for the preparation of a multiple branch peptide construct, said method comprising:
   a) supplying a core matrix having a plurality of amine moieties;
   b) attaching the matrix to a resin;
   c) constructing a plurality of branches of peptides on the matrix via solid phase stepwise elongation, whereby each peptide branch is covalently attached to the matrix at the amine moiety and contains the amino acid sequence Arg-Gln-Gly-Tyr(SEQ. ID. NO. 1) preceded by from 0 to 4 amino acid residues and succeeded by from 2 to 4 amino acid residues; and
   d) cleaving the matrix from the resin.

17. The method as recited in claim 16 wherein the resin is 4-oxymethyl-phenylacetamidomethyl copoly(styrene-1% divinylbenzene).

18. The method as recited in claim 16 wherein peptide branch elongation is effected by a Boc/benzyl process, including systematic double coupling with hydroxybenzotriazole active esters.

19. The method as recited in claim 16 wherein the cleavage from the resin is effected with anhydrous hydrogen fluoride at 0° C.

* * * * *

UNITED STATES PATENT AND TRADEMARK OFFICE
CERTIFICATE OF CORRECTION

PATENT NO. : 6,379,679 B1
DATED : June 11, 2002
INVENTOR(S) : Mabrouk et al.

It is certified that error appears in the above-identified patent and that said Letters Patent is hereby corrected as shown below:

<u>Title page,</u>
Item [73], please change the Assignee "Gellpep" to -- Cellpep --.

Signed and Sealed this

Sixteenth Day of July, 2002

*Attest:*

*Attesting Officer*

JAMES E. ROGAN
*Director of the United States Patent and Trademark Office*